(12) United States Patent
Kim et al.

(10) Patent No.: US 11,905,238 B2
(45) Date of Patent: Feb. 20, 2024

(54) METHOD FOR PREPARING 1-BUTENE AND PROPYLENE

(71) Applicant: LG CHEM, LTD., Seoul (KR)

(72) Inventors: In Seop Kim, Daejeon (KR); Sang Beom Lee, Daejeon (KR); Doo Wook Kim, Daejeon (KR); Man Woo Son, Daejeon (KR)

(73) Assignee: LG Chem, Ltd., Seoul (KR)

( * ) Notice: Subject to any disclaimer, the term of this patent is extended or adjusted under 35 U.S.C. 154(b) by 4 days.

(21) Appl. No.: 17/777,256

(22) PCT Filed: Jul. 12, 2021

(86) PCT No.: PCT/KR2021/008892
§ 371 (c)(1),
(2) Date: May 16, 2022

(87) PCT Pub. No.: WO2022/030784
PCT Pub. Date: Feb. 10, 2022

(65) Prior Publication Data
US 2022/0402837 A1 Dec. 22, 2022

(30) Foreign Application Priority Data

Aug. 7, 2020 (KR) .................. 10-2020-0099288

(51) Int. Cl.
*C07C 5/05* (2006.01)
*C07C 7/04* (2006.01)
(Continued)

(52) U.S. Cl.
CPC ............... *C07C 5/05* (2013.01); *B01D 3/143* (2013.01); *C07C 6/04* (2013.01); *C07C 7/08* (2013.01)

(58) Field of Classification Search
None
See application file for complete search history.

(56) References Cited

U.S. PATENT DOCUMENTS 6,075,173 A * 6/2000 Chodorge ................ C07C 6/04
585/277
6,358,482 B1 * 3/2002 Chodorge ................ C07C 6/04
422/131
(Continued)

FOREIGN PATENT DOCUMENTS

CN 104684873 A 6/2015
FR 3081461 A1 11/2019
(Continued)

OTHER PUBLICATIONS

T. Streich et al., HP Process Engineering and Optimization, "Secure the Best Benefits from C4 Hydrocarbon Processing—Part 1: Separation Sequences," Hydrocarbon Processing, XP 55457846A, Jun. 2016, (pp. 73-78).

*Primary Examiner* — Tam M Nguyen
(74) *Attorney, Agent, or Firm* — Bryan Cave Leighton Paisner LLP

(57) ABSTRACT

Provided is a method for preparing 1-butene and propylene including: supplying a C4 mixture stream to a first hydrogenation reactor to convert 1,3-butadiene into 1-butene; supplying a discharge stream from the first hydrogenation reactor to a first distillation column, supplying a lower discharge stream from the first distillation column including 2-butene and n-butane to a metathesis reactor, and supplying an upper discharge stream from the first distillation column including 1-butene and i-butane to a second distillation column; recovering an upper discharge stream the second distillation column including i-butane and recovering 1-butene from a lower discharge stream from the second distillation column; and producing propylene in the metathesis reactor, supplying a discharge stream from the metathesis reactor to a purification unit to recover propylene, and recycling an unreacted material to the metathesis reactor.

12 Claims, 2 Drawing Sheets

(51) Int. Cl.
*C07C 6/04* (2006.01)
*C07C 7/08* (2006.01)
*B01D 3/14* (2006.01)

(56) References Cited

U.S. PATENT DOCUMENTS

| | | | |
|---|---|---|---|
| 6,420,619 B1* | 7/2002 | Gartside | C07C 11/06 |
| | | | 208/143 |
| 7,459,593 B1 | 12/2008 | Krupa et al. | |
| 7,576,251 B2 | 8/2009 | Gartside et al. | |
| 7,601,309 B2 | 10/2009 | Krupa et al. | |
| 11,505,516 B2* | 11/2022 | Leal | C07C 41/06 |
| 2002/0183578 A1* | 12/2002 | Commereuc | C07C 11/06 |
| | | | 585/324 |
| 2004/0192994 A1 | 9/2004 | Bridges et al. | |
| 2004/0267067 A1* | 12/2004 | Bridges | C07C 5/2568 |
| | | | 585/324 |
| 2005/0043574 A1* | 2/2005 | Powers | C07C 11/06 |
| | | | 585/324 |
| 2005/0124839 A1* | 6/2005 | Gartside | B01J 21/08 |
| | | | 585/643 |
| 2006/0089517 A1 | 4/2006 | Podrebarac et al. | |
| 2006/0235253 A1* | 10/2006 | Gartside | C07C 7/04 |
| | | | 585/664 |
| 2009/0030252 A1 | 1/2009 | Senetar et al. | |
| 2014/0081061 A1 | 3/2014 | Stanley et al. | |
| 2021/0246386 A1* | 8/2021 | Koseoglu | C10G 45/54 |

FOREIGN PATENT DOCUMENTS

| | | |
|---|---|---|
| JP | 11-286459 A | 10/1999 |
| KR | 1987-0001082 B1 | 6/1987 |
| KR | 10-1998-0033193 A | 7/1998 |
| KR | 10-2007-0070185 A | 7/2007 |
| KR | 10-2010-0069156 A | 6/2010 |
| KR | 10-2014-0090691 A | 7/2014 |
| KR | 10-2017-0084076 A | 7/2017 |
| KR | 10-2021-0027788 A | 3/2021 |
| WO | 2019/016710 A1 | 1/2019 |

* cited by examiner

[FIG. 1]
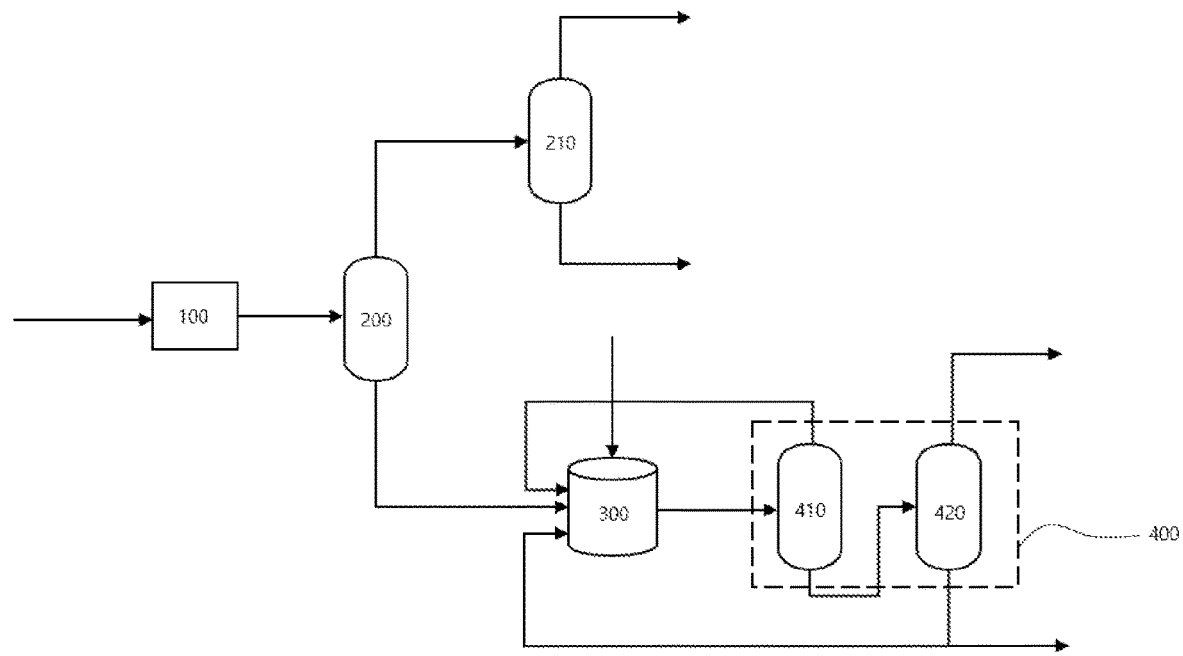
[FIG. 2]
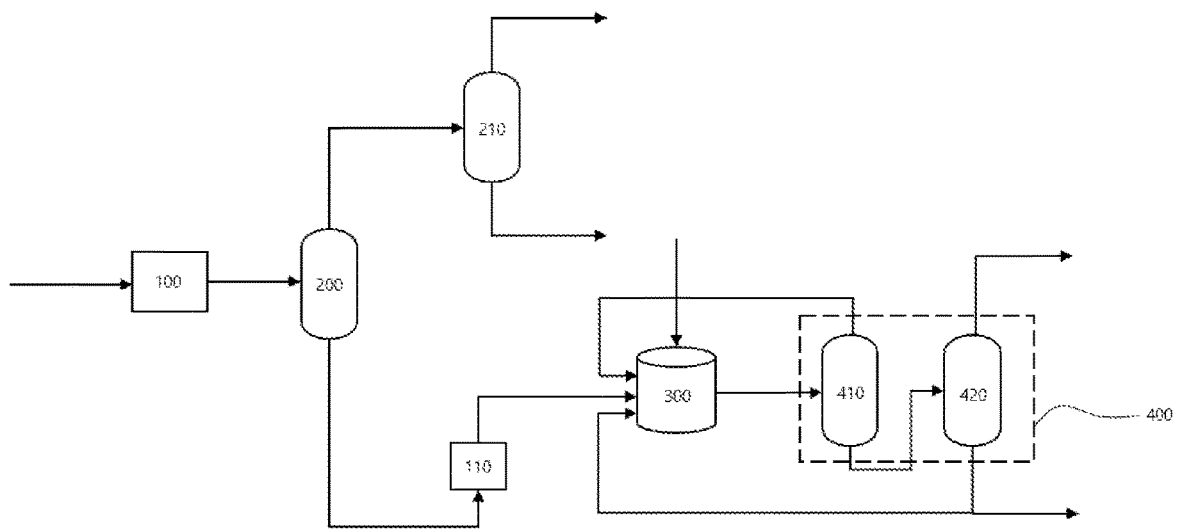

【FIG. 3】
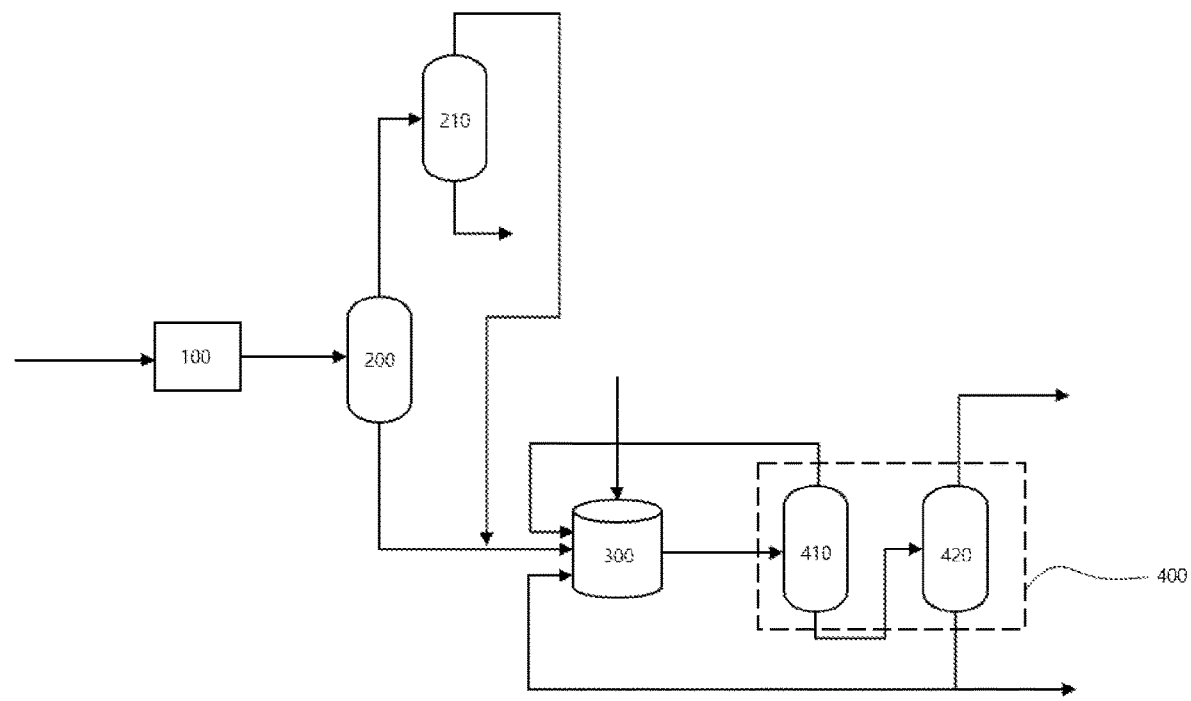
【FIG. 4】
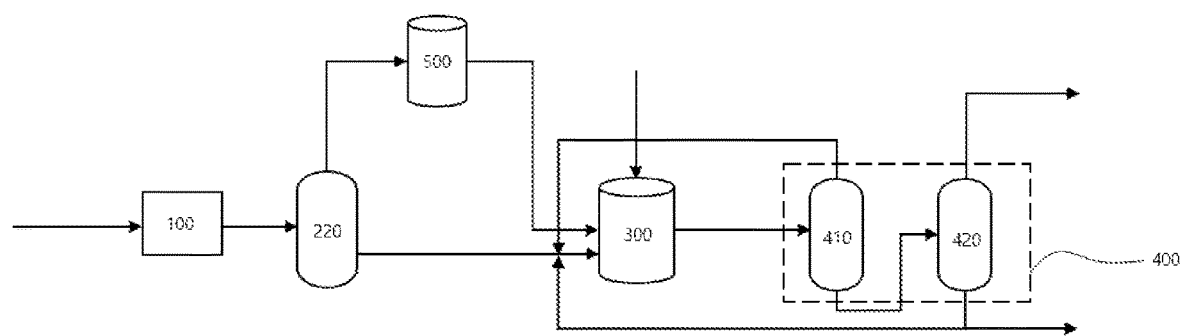

METHOD FOR PREPARING 1-BUTENE AND PROPYLENE

CROSS-REFERENCE TO RELATED APPLICATIONS

The present application is a National Phase entry pursuant to 35 U.S.C. § 371 of International Application No. PCT/KR2021/008892, filed on Jul. 12, 2021, and claims the benefit of and priority to Korean Patent Application No. 10-2020-0099288, filed on Aug. 7, 2020, the entire contents of which are incorporated by reference in their entirety for all purposes as if fully set forth herein.

TECHNICAL FIELD

The present invention relates to a method for preparing 1-butene and propylene, and more particularly, to a method for preparing i-butane together with 1-butene and propylene from a C4 mixture stream in one process.

BACKGROUND ART

Naphtha cracking is mainly used for producing by-products such as ethylene, propylene, butadiene, and a benzene-toluene-xylene (BTX) mixture by a method of supplying naphtha with steam at a high temperature and applying heat at 1,000° C. or higher to break a ring between carbons.

Here, a C4 hydrocarbon mixture (raw C4) including a single bond, a double bond, or a triple bond and including butadiene is separated by a series of purification processes.

Specifically, 1,3-butadiene which is useful as a raw material of a synthetic rubber is first separated from the C4 hydrocarbon mixture (raw C4) by extraction or extraction distillation. Raffinate-1 which remains after removing 1,3-butadiene from the mixture of a C4 hydrocarbon compound (raw C4) includes isobutene, 1-butene, 2-butene, n-butane, and i-butane with a trace of 1,3-butadiene.

When the raffinate-1 is reacted with methanol, isobutene and methanol react with each other to form methyl tertiary butyl ether (MTBE) and MTBE is separated from the raffinate-1 to separate isobutene from the raffinate-1. Raffinate-2 which remains after removing isobutene from the raffinate-1 includes 1-butene, 2-butene, n-butane, i-butane, and a trace of 1,3-butadiene.

The raffinate-2 including 1-butene, 2-butene, n-butane, i-butane, and a trace of 1,3-butadiene may be used for various applications, and among them, raffinate-2 may be used for producing propylene by metathesis.

Conventionally, in order to produce propylene using a raffinate-2 stream, 1-butene in a stream is isomerized to 2-butene to increase a content of 2-butene and then a reaction with ethylene is performed in a metathesis reactor to produce propylene.

In this case, since a large amount of 1-butene having a high commercial added value is isomerized to 2-butene, an economic loss is caused and a flow rate of a stream supplied to the metathesis reactor is high, and thus, it is difficult to increase the recycle flow rate of the metathesis reactor and there is a limitation in improving a propylene conversion rate.

DISCLOSURE

Technical Problem

An object of the present invention is to provide a method for preparing both 1-butene and propylene having a high commercial added value from a raffinate-2 stream including 1-butene, 2-butene, n-butane, i-butane, and a trace of 1,3-butadiene at the same time, in order to solve the problems mentioned in Background Art.

That is, in the present invention, a trace of 1,3-butadiene is removed from a raffinate-2 stream including 1-butene, 2-butene, n-butane, i-butane, and a trace of 1,3-butadiene, 1-butene is separated in high purity, and then a reaction with ethylene is performed in a metathesis reactor to produce propylene, and thus, 1-butene and propylene having a high commercial added value may be produced in a high purity.

Technical Solution

In one general aspect, a method for preparing 1-butene and propylene includes: supplying a C4 mixture stream to a first hydrogenation reactor to convert 1,3-butadiene into 1-butene; supplying a discharge stream from the first hydrogenation reactor to a first distillation column, supplying a lower discharge stream from the first distillation column including 2-butene and n-butane to a metathesis reactor, and supplying an upper discharge stream from the first distillation column including 1-butene and i-butane to a second distillation column; recovering an upper discharge stream the second distillation column including i-butane and recovering 1-butene from a lower discharge stream from the second distillation column; and producing propylene in the metathesis reactor, supplying a discharge stream from the metathesis reactor to a purification unit to recover propylene, and recycling an unreacted material to the metathesis reactor.

Advantageous Effects

According to the method for preparing 1-butene and propylene of the present invention, 1-butene is separated from a C4 mixture stream and then a reaction with ethylene is performed in a metathesis reactor to produce propylene, and thus, both 1-butene and propylene having a high commercial added value may be produced at the same time.

In addition, 1,3-butadiene in the C4 mixture stream is converted into 1-butene by a hydrogenation reaction before the separation of 1-butene, thereby separating 1-butene in a high purity, and also, preventing 1,3-butadiene from acting as a catalytic poison in a metathesis reaction.

In addition, the C4 mixture stream which has gone through the hydrogenation reaction is supplied to a first distillation column, and a lower discharge stream having a high content of 2-butene and low contents of 1-butene and 1,3-butadiene is separated in the first distillation column and supplied to a metathesis reactor to produce propylene, thereby removing an isomerization reactor and a hydrogenation reactor which are required in a conventional process of producing propylene using a C4 mixture.

In addition, an upper discharge stream from the first distillation column is supplied to a second distillation column, a high value-added 1-butene may be produced from a lower discharge stream from the second distillation column, and since an upper discharge stream may be sold as a separate i-butane product without being supplied to the metathesis reactor with the lower discharge stream from the first distillation column, an additional economic benefit may be obtained together with 1-butene and propylene.

DESCRIPTION OF DRAWINGS

FIGS. 1 and 2 are process flow diagrams according to a method for preparing 1-butene and propylene according to an exemplary embodiment of the present invention, respectively.

FIGS. 3 and 4 are process flow diagrams according to a method for preparing propylene according to the Comparative Examples, respectively.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

The term "stream" in the present invention may refer to a fluid flow in a process, or may refer to a fluid itself flowing in a pipe. Specifically, the "stream" may refer to both a fluid itself flowing in a pipe connecting each device and a fluid flow. In addition, the fluid may refer to a gas or a liquid.

The term "C# mixture" in the present invention, wherein "#" is a positive integer, refers to a mixture including all hydrocarbons having # carbon atoms. Therefore, the term "C4 mixture" refers to a mixture of hydrocarbon compounds having 4 carbon atoms.

Hereinafter, the present invention will be described in more detail referring to FIGS. 1 and 2, for better understanding of the present invention.

According to the present invention, a method for preparing 1-butene and propylene is provided. The method for preparing 1-butene and propylene may include: supplying a C4 mixture stream to a first hydrogenation reactor 100 to convert 1,3-butadiene into 1-butene; supplying a discharge stream from the first hydrogenation reactor 100 to a first distillation column 200, supplying a lower discharge stream from the first distillation column 200 including 2-butene and n-butane to a metathesis reactor 300, and supplying an upper discharge stream from the first distillation column 200 including 1-butene and i-butane to a second distillation column 210; recovering an upper discharge stream from the second distillation column 210 including i-butane and recovering 1-butene from a lower discharge stream from the second distillation column 210; and producing propylene in the metathesis reactor 300, supplying a discharge stream from the metathesis reactor 300 to a purification unit 400 to recover propylene, and recycling an unreacted material to the metathesis reactor 300.

According to an exemplary embodiment of the present invention, the C4 mixture stream may be a raffinate-2 stream separated from a naphtha cracking center (NCC).

The naphtha cracking is mainly used for producing by-products such as ethylene, propylene, butadiene, and a benzene-toluene-xylene (BTX) mixture by a method of supplying naphtha with steam at a high temperature and applying heat at 1,000° C. or higher to break a ring between carbons.

Here, a C4 hydrocarbon mixture (raw C4) including a single bond, a double bond, or a triple bond and including butadiene may be separated by a series of purification processes.

Specifically, 1,3-butadiene which is useful as a raw material of a synthetic rubber is first separated from the C4 hydrocarbon mixture (raw C4) by extraction or extraction distillation. Raffinate-1 which remains after removing 1,3-butadiene from the mixture of a C4 hydrocarbon compound (raw C4) may include isobutene, 1-butene, 2-butene, n-butane, and i-butane with a trace of 1,3-butadiene.

When the raffinate-1 is reacted with methanol, isobutene and methanol react with each other to form methyl tertiary butyl ether (MTBE), and MTBE is separated from the raffinate-1 to separate isobutene from the raffinate-1. Raffinate-2 which remains after removing isobutene from the raffinate-1 may include 1-butene, 2-butene, n-butane, i-butane, and a trace of 1,3-butadiene. Consequently, the C4 mixture may include one or more selected from the group consisting of n-butane, i-butane, 1,3-butadiene, 1-butene, and 2-butene. Specifically, the C4 mixture may include all of n-butane, i-butane, 1,3-butadiene, 1-butene, and 2-butene.

According to an exemplary embodiment of the present invention, a content of 1,3-butadiene in the C4 mixture stream is 1 wt % or less, which is a very small amount. However, since a boiling point of 1,3-butadiene is about −4.4° C. and a boiling point of 1-butene is −6.2° C., a difference in their boiling points is small, and thus, it is difficult to separate them by distillation. Therefore, when the trace of 1,3-butadiene is included in the C4 mixture stream, it is difficult to separate high-purity 1-butene.

In addition, the trace of 1,3-butadiene acts as a catalytic poison in the metathesis reactor 300 in which propylene is produced by a metathesis reaction of 2-butene and ethylene, thereby preventing conversion into propylene.

In this regard, the present invention may further include, before producing 1-butene and 2-butene, a step of supplying the C4 mixture stream to the first hydrogenation reactor 100 to convert 1,3-butadiene into 1-butene. Thus, 1,3-butadiene which is included in a trace in the C4 mixture stream may be removed to improve a purity of 1-butene and improve a conversion rate of propylene.

The first hydrogenation reactor 100 performs a selective hydrogenation reaction of 1,3-butadiene included in the C4 mixture stream to convert 1,3-butadiene into 1-butene. For example, a temperature of the hydrogenation reaction may be in a range of 30° C. to 100° C., 30° C. to 80° C., or 30° C. to 60° C., and a reaction pressure may be in a range of 10 KG to 80 KG, 15 KG to 60 KG, or 20 KG to 40 KG.

According to an exemplary embodiment of the present invention, the C4 mixture stream is supplied to the first hydrogenation reactor 100 to convert 1,3-butadiene into 1-butene, whereby the content of 1,3-butadiene in the discharge stream from the first hydrogenation reactor 100 may be 0.1 wt % or less. For example, the content of 1,3-butadiene in the discharge stream from the first hydrogenation reactor 100 may be 0 wt % to 0.1 wt %, 0 wt % to 0.01 wt %, or 0 wt % to 0.001 wt %. 1-butene and propylene are produced from the C4 mixture stream including 1,3-butadiene within the range, thereby producing 1-butene in a high purity and propylene at a high conversion rate.

According to an exemplary embodiment of the present invention, the C4 mixture stream is supplied to the first hydrogenation reactor 100 to convert 1,3-butadiene into 1-butene, whereby the content of 1-butene in the discharge stream from the first hydrogenation reactor 100 may be increased. Specifically, the content of 1-butene in the discharge stream from the first hydrogenation reactor 100 may be higher than the content of 1-butene in the C4 mixture stream by 1 wt % or more. For example, the content of 1-butene in the discharge stream from the first hydrogenation reactor 100 may be higher than the content of 1-butene in the C4 mixture stream by 1 wt % to 5 wt %, 1 wt % to 4 wt %, or 1 wt % to 3 wt %. As the content of 1-butene in the discharge stream from the first hydrogenation reactor 100 is increased, the content and purity of 1-butene separated in the second distillation column 210 may be improved.

As such, before producing 1-butene and propylene, the C4 mixture stream is supplied to the first hydrogenation reactor 100 to convert 1,3-butadiene into 1-butene, thereby implementing an effect from an increased content of 1-butene together with an effect from removal of 1,3-butadiene.

According to an exemplary embodiment of the present invention, the discharge stream from the first hydrogenation reactor 100 may include n-butane, i-butane, 1-butene, and 2-butene. In general, the content of 1-butene is higher than the content of 2-butene in the C4 mixture produced from naphtha cracking. The discharge stream from the first hydrogenation reactor 100 including n-butane, i-butane, 1-butene, and 2-butene is supplied to the first distillation column 200, and n-butane and 2-butene which are relatively heavy may be separated as a lower discharge stream by distillation and i-butane and 1-butene which are relatively light may be separated as an upper discharge stream.

The first distillation column 200 may have controlled operation temperature and operation pressure, in order to separate the upper discharge stream including i-butane and 1-butene and the lower discharge stream including n-butane and 2-butene. For example, the operation temperature of the first distillation column 200 may be −5° C. to 140° C., −5° C. to 100° C., or −5° C. to 60° C. In addition, the operation pressure of the first distillation column 200 may be atmospheric pressure to 30 kg/cm$^2$g, atmospheric pressure to 10 kg/cm$^2$g, or atmospheric pressure to 5 kg/cm$^2$g. The first distillation column 200 is controlled to the operation temperature and the operation pressure within the range, thereby effectively separating the upper discharge stream including i-butane and 1-butene and a lower discharge stream including n-butane and 2-butene.

According to an exemplary embodiment of the present invention, the upper discharge stream from the first distillation column 200 includes i-butane and 1-butene, and the stream may be supplied to the second distillation column 210 for separating each of i-butane and 1-butene. Specifically, in the second distillation column 210, the operation temperature and the operation pressure may be controlled for separating each of i-butane and 1-butene. For example, the operation temperature of the second distillation column 210 may be −15° C. to 130° C., −15° C. to 80° C., or −15° C. to 45° C. In addition, the operation pressure of the second distillation column 210 may be atmospheric pressure to 30 kg/cm$^2$g, atmospheric pressure to 10 kg/cm$^2$g, or atmospheric pressure to 5 kg/cm$^2$g. The second distillation column 210 is controlled to the operation temperature and the operation pressure within the range, thereby separating each of i-butane and 1-butene in a high purity.

The second distillation column 210 is supplied with the upper discharge stream from the first distillation column 200, and may separate relatively light i-butane from the upper discharge stream and separate relatively heavy 1-butene from the lower discharge stream.

The content of 1-butene in the lower discharge stream from the second distillation column may be, for example, 98 wt % or more. For example, the content of 1-butene in the lower discharge stream from the second distillation column 210 may be 98 wt % to 100 wt % or 99 wt % to 100 wt %. The lower discharge stream from the second distillation column 210 including 1-butene at the content within the range is separated, thereby producing high-purity 1-butene.

In addition, the upper discharge stream from the second distillation column 210 including i-butane is not supplied to the metathesis reactor 300 with the lower discharge stream from the first distillation column 200 including n-butane and 2-butene, but is recovered and may be sold as a separate i-butane product. For example, the i-butane may be sold as an additive for increasing an octane number of gasoline in an oil refinery. As such, i-butane is produced and sold from the C4 mixture in addition to 1-butene and propylene, thereby obtaining an additional economic benefit. In addition, since the upper discharge stream from the second distillation column 210 including i-butane is not supplied to the metathesis reactor 300 with the lower discharge stream from the first distillation column 200, a distillation column for separating light materials which is required in the conventional process of producing propylene using the C4 mixture may be removed to simplify the process.

In addition, according to an exemplary embodiment of the present invention, the lower discharge stream from the first distillation column 200 may be supplied to the metathesis reactor for producing propylene using 2-butene. For example, the lower discharge stream from the first distillation column 200 may include 40 wt % to 70 wt %, 45 wt % to 70 wt %, or 50 wt % to 70 wt % of 2-butene. In addition, the lower discharge stream from the first distillation column 200 may include 0.1 wt % to 15 wt %, 0.1 wt % to 13 wt %, or 0.1 wt % to 10 wt % of 1-butene. As such, the lower discharge stream from the first distillation column 200 having a high content of 2-butene and almost no 1-butene and 1,3-butadiene is directly supplied to the metathesis reactor 300 to produce propylene by a metathesis reaction, thereby removing an isomerization reactor which is required for converting 1-butene into 2-butene and removing 1,3-butadiene in the conventional process of producing propylene using the C4 mixture, and an additional hydrogenation reactor to simplify the process and reduce costs. In addition, as such, the stream excluding 1-butene and i-butane from the first distillation column 200 is supplied to the metathesis reactor 300, thereby decreasing the flow rate supplied to the metathesis reactor 300 to increase the flow rate of the unreacted material stream recycled to the metathesis reactor 300, and thus, a conversion rate of propylene in the metathesis reactor 300 may be improved.

If necessary, the lower discharge stream from the first distillation column 200 may be supplied to the metathesis reactor 300 after passing through the second hydrogenation reactor 110. The second hydrogenation reactor may be supplied with the lower discharge stream from the first distillation column 200 to convert a trace of 1-butene included in the lower discharge stream from the first distillation column 200 into 2-butene. Also, the second hydrogenation reactor 110 removes impurities which acts as a catalytic poison in the lower discharge stream from the first distillation column 200 to prevent deterioration of catalytic performance in the metathesis reactor 300. Thus, when the discharge stream from the second hydrogenation reactor 110 from which the catalytic poison is removed and which has a further increased content of 2-butene is supplied to the metathesis reactor 300 to produce propylene, the conversion rate of propylene may be further increased.

In the second hydrogenation reactor 110, a hydrogenation reaction temperature may be for example, in a range of 30° C. to 120° C., 40° C. to 100° C., or 50° C. to 80° C., and a reaction pressure may be in a range of 5 KG to 40 KG, 5 KG to 30 KG, or 5 KG to 20 KG.

The metathesis reactor 300 may be a reactor in which 2-butene included in the supplied lower discharge stream from the first distillation column 200 and an ethylene monomer separately supplied are reacted to produce propylene. Here, n-butane included in the lower discharge stream from the first distillation column 200 may act as an inert material in a propylene preparation reaction.

The metathesis reaction may be carried out under heterogeneous conditions. If necessary, the metathesis reaction may be carried out under pressure. For example, the metathesis reaction may be carried out under a pressure in a range of 1 KG to 100 KG, 5 KG to 70 KG, or 10 KG to 50 KG. In addition, the metathesis reaction may be carried out at a temperature in a range of 250° C. to 500° C., 250° C. to 400° C., or 250° C. to 350° C.

The metathesis reaction may be performed in the presence of a catalyst. The catalyst may include, for example, one or more selected from the group consisting of transition metals and oxides thereof. The transition metal may include, for example, tungsten, molybdenum, rhenium, and the like. If necessary, the catalyst may be used in the form of being supported on a silica carrier.

In addition, if necessary, a diluent which is inert under reaction conditions may be used. The diluent may include, for example, paraffin-based or cycloparaffin-based hydrocarbons.

Conventionally, in order to produce propylene using the C4 mixture stream, a large amount of 1-butene in a stream is isomerized to 2-butene to increase a content of 2-butene, which is then reacted with the ethylene monomer in the metathesis reactor 300 to produce propylene. However, the present invention solves a problem arising from 1,3-butadiene and increases 1-butene by converting a trace of 1,3-butadiene from the C4 mixture stream into 1-butene, and the high value-added 1-butene is separated individually without being isomerized to 2-butene and used in the preparation of propylene, thereby improving economic feasibility.

As such, after a trace of 1,3-butadiene is removed and a high value-added 1-butene is separated, the lower discharge stream from the first distillation column 200 including 2-butene is supplied to the metathesis reactor 300 to react the stream with the ethylene monomer separately supplied to the metathesis reactor 300, thereby producing propylene.

The discharge stream from the metathesis reactor 300 may include an unreacted material which does not participate in a propylene preparation reaction. Therefore, the discharge stream from the metathesis reactor 300 is supplied to the purification unit 400 to separate each of propylene and the unreacted material. Here, the unreacted material separated from the purification unit 400 may include an unreacted C4 mixture including an unreacted ethylene monomer, n-butane, and 2-butene, and may be recycled to the metathesis reactor 300.

According to an exemplary embodiment of the present invention, the purification unit 400 may include one or more purification columns. For example, the purification unit 400 may be formed of a first purification column 410 and a second purification column 420, that is, two purification columns.

The discharge stream from the metathesis reactor 300 may be supplied to the first purification column 410 of the purification unit 400. The first purification column 410 may separate a light unreacted ethylene monomer from the upper discharge stream and recycle the monomer to the metathesis reactor 300. In addition, the unreacted ethylene monomer may be separated in the first purification column 410 and the remaining components may be supplied to the second purification column 420 as the lower discharge stream. Here, the unreacted ethylene monomer recycled to the metathesis reactor 300 may participate in the propylene preparation reaction again. As such, the unreacted ethylene may be reused to reduce manufacturing costs.

In the first purification column 410, an operation temperature and an operation pressure may be controlled for effectively separating the unreacted ethylene monomer from the discharge stream from the metathesis reactor 300. Specifically, the operation pressure of the first purification column 410 may be 10 KG to 50 KG, 10 KG to 40 KG, or 20 KG to 30 KG, and the operation temperature thereof may be 10° C. to 150° C., 10° C. to 130° C., or 20° C. to 100° C.

In the second purification column 420, propylene is recovered from the upper discharge stream, an unreacted C4 mixture including heavy n-butane and 2-butene may be separated from the lower discharge stream and recycled to the metathesis reactor 300. Here, 2-butene in the recycled unreacted C4 mixture may participate in the propylene preparation reaction again.

The content of propylene in the upper discharge stream from the second purification column 420 may be 95 wt % to 100 wt %, 96 wt % to 100 wt %, or 97 wt % to 100 wt %. As such, when 1-butene and propylene are produced by the method according to the present invention, each component may be produced in a high purity.

In the second purification column 420, an operation temperature and an operation pressure may be controlled for effectively separating propylene from the lower discharge stream from the first purification column 410. Specifically, the operation pressure of the second purification column 420 may be 1 KG to 40 KG, 1 KG to 30 KG, or 10 KG to 20 KG, and the operation temperature thereof may be 20° C. to 150° C., 30° C. to 130° C., or 40° C. to 110° C.

Hereinabove, the method for preparing 1-butene and propylene according to the present invention has been described and illustrated in the drawings, but the description and the illustration in the drawings are the description and the illustration of only core constitutions for understanding of the present invention, and in addition to the process and devices described above and illustrated in the drawings, the process and the devices which are not described and illustrated separately may be appropriately applied and used for carrying out the method for preparing 1-butene and propylene according to the present invention.

Hereinafter, the present invention will be described in more detail by the Examples. However, the following Examples are provided for illustrating the present invention, and it is apparent to a person skilled in the art that various modifications and alterations may be made without departing from the scope and spirit of the present invention and the scope of the present invention is not limited thereto.

EXAMPLE

Example 1

For the process flow diagram illustrated in FIG. 1, the process was simulated using an Aspen Plus simulator from Aspen Technology, Inc.

Specifically, a C4 mixture stream (C4 Raffinate-2) including 1-butene, 2-butene, n-butane, i-butane, and a trace of 1,3-butadiene was supplied to a first hydrogenation reactor 100 to convert a trace of 1,3-butadiene into 1-butene.

A discharge stream from the first hydrogenation reactor 100 was supplied to a first distillation column 200, an upper discharge stream from the first distillation column 200 was supplied to a second distillation column 210, and a lower discharge stream from the first distillation column was supplied to a metathesis reactor 300.

In the second distillation column 210, i-butane was separated from the upper discharge stream and 1-butene was separated from the lower discharge stream. Here, a purity of 1-butene separated was confirmed to be 99.1%.

The metathesis reactor 300 was supplied with an ethylene monomer stream separately supplied, and the ethylene monomer and 2-butene in the lower discharge stream from the first distillation column 200 were reacted to produce propylene.

A discharge stream from the metathesis reactor 300 completing the reaction was supplied to a first purification column 410 and an unreacted ethylene monomer was separated from an upper discharge stream and recycled to the metathesis reactor 300. In addition, a lower discharge stream from the first purification column 410 was supplied to a second purification column 420.

The second purification column 420 was supplied with the lower discharge stream from the first purification column 410, propylene was separated from the upper discharge stream, and an unreacted C4 mixture was separated from the lower discharge stream, partially purged, and recycled to the metathesis reactor 300.

Here, it was confirmed that the flow rate of the C4 mixture stream supplied to the first hydrogenation reactor was 40.0 ton/hr, the flow rate of the stream supplied to the metathesis reactor 300 was 20.8 ton/hr, the flow rate of the ethylene stream supplied to the metathesis reactor 300 was 17.6 ton/hr, and the flow rate of the unreacted C4 mixture recycled to the metathesis reactor 300 in the second purification column 420 was 23.2 ton/hr.

Example 2

For the process flow diagram illustrated in FIG. 2, the process was simulated using an Aspen Plus simulator from Aspen Technology, Inc.

Specifically, a C4 mixture stream (C4 Raffinate-2) including 1-butene, 2-butene, n-butane, i-butane, and a trace of 1,3-butadiene was supplied to the first hydrogenation reactor 100 to convert a trace of 1,3-butadiene into 1-butene.

A discharge stream from the first hydrogenation reactor 100 was supplied to the first distillation column 200, an upper discharge stream from the first distillation column 200 was supplied to the second distillation column 210, and a lower discharge stream from the first distillation column was supplied to a second hydrogenation reactor 110.

In the second distillation column 210, i-butane was separated from the upper discharge stream and 1-butene was separated from the lower discharge stream. Here, a purity of 1-butene separated was confirmed to be 99.1%.

In the second hydrogenation reactor 110, a catalytic poison of a lower discharge stream from the first distillation column 200 was completely removed, a trace of 1-butene was converted into 2-butene, and a discharge stream from the second hydrogenation reactor 110 was supplied to the metathesis reactor 300.

The metathesis reactor 300 was supplied with an ethylene monomer stream separately supplied, and the ethylene monomer and 2-butene in the lower discharge stream from the first distillation column 200 were reacted to produce propylene.

A discharge stream from the metathesis reactor 300 completing the reaction was supplied to the first purification column 410 and an unreacted ethylene monomer was separated from an upper discharge stream and recycled to the metathesis reactor 300. In addition, a lower discharge stream from the first purification column 410 was supplied to a second purification column 420.

The second purification column 420 was supplied with the lower discharge stream from the first purification column 410, propylene was separated from the upper discharge stream, and an unreacted C4 mixture was separated from the lower discharge stream, partially purged, and recycled to the metathesis reactor 300.

Here, it was confirmed that the flow rate of the C4 mixture stream supplied to the first hydrogenation reactor was 40.0 ton/hr, the flow rate of the stream supplied to the metathesis reactor 300 was 20.8 ton/hr, the flow rate of the ethylene stream supplied to the metathesis reactor 300 was 17.6 ton/hr, and the flow rate of the unreacted C4 mixture recycled to the metathesis reactor 300 in the second purification column 420 was 23.2 ton/hr.

COMPARATIVE EXAMPLE

Comparative Example 1

For the process flow diagram illustrated in FIG. 3, the process was simulated using an Aspen Plus simulator from Aspen Technology, Inc.

Specifically, a C4 mixture stream (C4 Raffinate-2) including 1-butene, 2-butene, n-butane, i-butane, and a trace of 1,3-butadiene was supplied to the first hydrogenation reactor 100 to convert a trace of 1,3-butadiene into 1-butene.

A discharge stream from the first hydrogenation reactor 100 was supplied to the first distillation column 200, an upper discharge stream from the first distillation column 200 was supplied to the second distillation column 210, and a lower discharge stream from the first distillation column was supplied to the metathesis reactor 300.

In the second distillation column 210, an upper discharge stream was supplied to the metathesis reactor 300 with a lower discharge stream from the first distillation column 200, and 1-butene was separated from the lower discharge stream. Here, a purity of 1-butene separated was confirmed to be 99.1%.

The metathesis reactor 300 was supplied with an ethylene monomer stream separately supplied, and the ethylene monomer and 2-butene were reacted to produce propylene.

A discharge stream from the metathesis reactor 300 completing the reaction was supplied to the first purification column 410 and an unreacted ethylene monomer was separated from an upper discharge stream and recycled to the metathesis reactor 300. In addition, a lower discharge stream from the first purification column 410 was supplied to a second purification column 420.

The second purification column 420 was supplied with the lower discharge stream from the first purification column 410, propylene was separated from the upper discharge stream, and an unreacted C4 mixture was separated from the lower discharge stream, partially purged, and recycled to the metathesis reactor 300.

Here, it was confirmed that the flow rate of the C4 mixture stream supplied to the first hydrogenation reactor was 40.0 ton/hr, the flow rate of the stream supplied to the metathesis reactor 300 was 23.2 ton/hr, the flow rate of the ethylene stream supplied to the metathesis reactor 300 was 17.6 ton/hr, and the flow rate of the unreacted C4 mixture recycled to the metathesis reactor 300 in the second purification column 420 was 20.8 ton/hr.

Comparative Example 2

For the process flow diagram illustrated in FIG. 4, the process was simulated using an Aspen Plus simulator from Aspen Technology, Inc.

Specifically, a C4 mixture stream including 1-butene, 2-butene, n-butane, i-butane, and a trace of 1,3-butadiene was supplied to a 1-butene separation column 220, a lower discharge stream from the 1-butene separation column 220 was supplied to the metathesis reactor 300, and an upper discharge stream including 1-butene was supplied to an isomerization reactor 500 to isomerize 1-butene to 2-butene, which was then supplied to the metathesis reactor 300.

The metathesis reactor 300 was supplied with an ethylene monomer stream separately supplied, and the ethylene monomer and 2-butene were reacted to produce propylene.

A discharge stream from the metathesis reactor 300 completing the reaction was supplied to the first purification column 410 and an unreacted ethylene monomer was separated from an upper discharge stream and recycled to the metathesis reactor 300. In addition, a lower discharge stream from the first purification column 410 was supplied to a second purification column 420.

The second purification column 420 was supplied with the lower discharge stream from the first purification column 410, propylene was separated from the upper discharge stream, and an unreacted C4 mixture was separated from the lower discharge stream, partially purged, and recycled to the metathesis reactor 300.

Here, it was confirmed that the flow rate of the C4 mixture stream supplied to the first hydrogenation reactor was 40.0 ton/hr, the flow rate of the stream supplied to the metathesis reactor 300 was 39.0 ton/hr, the flow rate of the ethylene stream supplied to the metathesis reactor 300 was 17.6 ton/hr, and the flow rate of the unreacted C4 mixture recycled to the metathesis reactor 300 in the second purification column 420 was 5.0 ton/hr.

Experimental Examples

In the processes of production of Examples 1 and 2 and Comparative Examples 1 and 2, a propylene conversion rate (%) in the metathesis reactor 300, a produced amount of 1-butene (ton/hr), a produced amount of propylene (ton/hr), and a produced amount of i-butane (ton/hr) were measured and are shown in the following Table 1.

TABLE 1

|  | Propylene conversion rate | Produced amount of 1-butene | Produced amount of propylene | Produced amount of i-butane |
| --- | --- | --- | --- | --- |
| Example 1 | 74.1 | 15.8 | 16.5 | 4.0 |
| Example 2 | 74.1 | 15.8 | 16.5 | 4.0 |
| Comparative Example 1 | 74.8 | 15.8 | 16.1 | — |
| Comparative Example 2 | 57.3 | — | 26.0 | — |

Referring to Table 1, the propylene conversion rate of Examples 1 and 2 in which i-butane was produced together with 1-butene and propylene by the method according to the present invention was 74.1%, and this was confirmed to be a result of separating 1-butene and i-butane from the C4 mixture stream before supplying the C4 mixture stream to the metathesis reactor 300, thereby decreasing the flow rate supplied to the metathesis reactor 300 to increase the flow rate of the unreacted C4 mixture recycled to the metathesis reactor 300 in the second purification column 420. In addition, in Example 2 in which the lower discharge stream from the first distillation column 200 passed through the second hydrogenation reactor 110 and was supplied to the metathesis reactor 300, it was confirmed that a catalytic poison was completely removed and the content of 2-butene was rather increased to the produced amount of propylene was increased.

In comparison, in Comparative Example 1 in which the upper discharge stream from the second distillation column 210 was supplied to the metathesis reactor 300 with the lower discharge stream from the first distillation column 200, it was confirmed that since i-butane was supplied to the metathesis reactor 300, a propylene conversion rate was increased due to a decrease in a concentration of 2-butene in the stream supplied to the metathesis reactor 300, but the produced amount of propylene was decreased. In addition, an economic benefit which may be obtained when i-butane is separated individually may not be expected.

In addition, in Comparative Example 2 in which the discharge stream from the first hydrogenation reactor 100 was supplied to a 1-butene separation device to separate the stream into a stream having a high content of 1-butene and a stream having a high content of 2-butene, and the stream having a high content of 1-butene was supplied to an isomerization reactor 500 to be isomerized to 2-butene, which was supplied to the metathesis reactor 300 with the stream having a high content of 2-butene, 1-butene having a higher price than propylene was isomerized to 2-butene which participated in the metathesis reaction to produce propylene, thereby lowering economic feasibility. In addition, an economic benefit which may be obtained when i-butane is separated individually may not be expected.

The invention claimed is:

1. A method for preparing 1-butene and propylene, the method comprising:
   supplying a C4 mixture stream to a first hydrogenation reactor to convert 1,3-butadiene into 1-butene without isomerizing 1-butene to 2-butene;
   supplying a discharge stream from the first hydrogenation reactor to a first distillation column, supplying a lower discharge stream from the first distillation column including 2-butene and n-butane to a metathesis reactor, and supplying an upper discharge stream from the first distillation column including 1-butene and i-butane to a second distillation column;
   recovering an upper discharge stream from the second distillation column including i-butane and recovering 1-butene from a lower discharge stream from the second distillation column; and
   producing propylene in the metathesis reactor, supplying a discharge stream from the metathesis reactor to a purification unit to recover propylene, and recycling an unreacted material to the metathesis reactor.

2. The method for preparing 1-butene and propylene of claim 1, wherein the C4 mixture stream includes one or more compounds selected from the group consisting of n-butane, i-butane, 1,3-butadiene, 1-butene, and 2-butene.

3. The method for preparing 1-butene and propylene of claim 1, wherein a content of 1,3-butadiene in the discharge stream from the first hydrogenation reactor is 0.1 wt % or less.

4. The method for preparing 1-butene and propylene of claim 1, wherein the lower discharge stream from the first distillation column includes 40 wt % to 70 wt % of 2-butene and 0.1 wt % to 15 wt % of 1-butene.

5. The method for preparing 1-butene and propylene of claim 1, wherein an operation temperature of the first distillation column is −5° C. to 140° C. and an operation pressure of the first distillation column is atmospheric pressure to 30 kg/cm$^2$g.

6. The method for preparing 1-butene and propylene of claim 1, wherein a content of 1-butene in the lower discharge stream from the second distillation column is 98 wt % or more.

7. The method for preparing 1-butene and propylene of claim 1, wherein an operation temperature of the second distillation column is −15° C. to 130° C. and an operation pressure of the second distillation column is atmospheric pressure to 30 kg/cm$^2$g.

8. The method for preparing 1-butene and propylene of claim 1, wherein the lower discharge stream from the first distillation column passes through a second hydrogenation reactor and then is supplied to the metathesis reactor.

9. The method for preparing 1-butene and propylene of claim 1, wherein in the metathesis reactor, the 2-butene included in the supplied lower discharge stream from the first distillation column and an ethylene monomer which is supplied separately are reacted to produce propylene.

10. The method for preparing 1-butene and propylene of claim 1, wherein the purification unit includes one or more purification columns.

11. The method for preparing 1-butene and propylene of claim 10,
wherein the purification unit includes a first purification column and a second purification column,
wherein the discharge stream from the metathesis reactor is supplied to the first purification column, an upper discharge stream from the first purification column including an unreacted ethylene monomer is recycled to the metathesis reactor, and a lower discharge stream from the first purification column is supplied to the second purification column, and
wherein propylene is recovered from an upper discharge stream from the second purification column and a lower discharge stream from the second purification column including an unreacted C4 mixture is recycled to the metathesis reactor.

12. The method for preparing 1-butene and propylene of claim 11, wherein a content of propylene in the upper discharge stream from the second purification column is 95 wt % or more.

* * * * *